(12) United States Patent
Brothers

(10) Patent No.: US 6,479,725 B1
(45) Date of Patent: Nov. 12, 2002

(54) METHOD OF TREATMENT OF A WOUND OR INCISION

(76) Inventor: Lisa M. Brothers, 26284 W. Vista Ct., Ingleside, IL (US) 60041

(*) Notice: Subject to any disclaimer, the term of this patent is extended or adjusted under 35 U.S.C. 154(b) by 133 days.

(21) Appl. No.: 09/609,654

(22) Filed: Jun. 30, 2000

(51) Int. Cl.[7] .......................... A61F 13/00; A61K 31/79
(52) U.S. Cl. .......................... 602/54; 602/42; 606/213; 606/214; 424/78.25; 424/78.31; 424/78.32; 424/78.36
(58) Field of Search ................... 424/443, 448, 424/449, 484, 485, 486, 78.06; 514/562, 563, 442, 617, 628, 118; 602/41–59; 128/888, 889; 606/213, 214

(56) References Cited

U.S. PATENT DOCUMENTS

| | | | |
|---|---|---|---|
| 5,259,835 A | 11/1993 | Clark et al. | 602/48 |
| 5,306,490 A | 4/1994 | Barley, Jr. | 424/78.35 |
| 5,328,687 A | 7/1994 | Leung et al. | 424/78.35 |
| 5,445,597 A | 8/1995 | Clark et al. | 602/48 |
| 5,514,372 A | 5/1996 | Leung et al. | 424/78.35 |
| 5,575,997 A | 11/1996 | Leung et al. | 424/78.35 |
| 5,582,834 A | 12/1996 | Leung et al. | 424/426 |
| 5,630,430 A | 5/1997 | Shultz et al. | 128/888 |
| 5,637,080 A | 6/1997 | Geng | 602/58 |
| 5,730,994 A | 3/1998 | Askill et al. | 424/402 |
| 5,780,048 A | 7/1998 | Lee | 424/443 |
| 5,807,563 A | 9/1998 | Askill et al. | 424/402 |
| 5,928,611 A | 7/1999 | Leung | 422/131 |
| 5,957,877 A | 9/1999 | Askill et al. | 602/54 |
| 5,960,795 A | 10/1999 | Schultz | 128/888 |
| 5,981,621 A | 11/1999 | Clark et al. | 523/118 |
| 6,001,345 A | 12/1999 | Askill et al. | 424/78.25 |
| 6,008,429 A | 12/1999 | Ritger | 602/57 |
| 6,010,714 A | 1/2000 | Leung et al. | 424/448 |
| 6,043,408 A | 3/2000 | Geng | 602/58 |
| 6,090,397 A | 7/2000 | Lee et al. | 424/405 |

OTHER PUBLICATIONS

"Superglue—Replaces Sutures." Dermatology Today; Nov. 2001.

"Glue is better than Sutures For Facial lacerations in Children" Manchester Royal Infirmary, Mar. 1, 2000; Best Bets.

Vetbond Tissue Adhesive; World Precision Instruments; 2002.

Tissumend; Veterinary Products Laboratories 2002.

Nexaband; Veterinary Products Laboratories 2001.

Glu Stitch; Glu Stitch, Inc.

Dermabond Topical Skin Adhesive, Ethicon, Inc., 1998.

(List continued on next page.)

Primary Examiner—Kim M. Lewis
(74) Attorney, Agent, or Firm—Foley & Lardner

(57) ABSTRACT

A method for forming an incision or wound dressing. First, second, and third layers 2-octyl cyanoacrylate adhesive 18, 20, and 22 are applied to a wound or incision site 14, with each layer covering the site 14 and extending to at least about five millimeters from each side of the site 14. After the first, second, and third layers 18, 20, and 22 are allowed to polymerize, a fourth layer 24 of 2-octyl cyanoacrylate adhesive is applied, the fourth layer 24 substantially covering at least one millimeter of the extending edge of the first, second, and third layers 18, 20, and 22. In the case of a high-tension wound or a wound near a joint, the fourth layer 24 extends at least about ten millimeters from each side of the site 14, and a fifth layer 26 of 2-octyl cyanoacrylate adhesive is applied. The fifth layer 26 substantially covers at least one millimeter of the extending edge of the first, second, and third layers 18, 20, and 22 and extends from each side of the site 14 a distance less than the distance the fourth layer 24 extends from each side of the site

28 Claims, 1 Drawing Sheet

OTHER PUBLICATIONS

Evaluation and Management of Traumatic Lacerations, Adam J. Singer, M.D. et al., New England Journal of Medicine 337:1142–1148 (Oct. 16, 1997).

A Prospective Comparison of Octylcyanoacrylate Tissue Adhesive and Suture for the Closure of Head and Neck Incisions, Maw, M.D. et al.; Journal of Otolaryngology, vol. 26 No. 1, 1997.

A Randomized Trial Comparing Octylcyanoacrylate Tissue Adhesive and Sutures in the Management of Lacerations, J. Quinn et al., JAMA, May 21, 1997.

Prospective, Randomized, Controlled Trial of Tissue Adhesive (2–Octylcyanoacrylate vs. Standard Wound Closure Techniques for Laceration Repair) Singer et al., Academic Emergency Medicine 1998 Cyanoacrylate Tissue Adhesives, Maw et al., American Journal of Cosmetic Surgery, vol. 14 No. 4, 1997.

A New Tissue Adhesive for Laceration Repair in Children, Bruns et al., Pediatric Academic Societies Meeting, Washington, D.C., May 2–6, 1997.

A Complete Guide for Using Dermabond, Ethicon, Inc. 1998.

METHOD OF TREATMENT OF A WOUND OR INCISION

TECHNICAL FIELD

This invention relates generally to the treatment of a wound or incision. More particularly, this invention relates to the treatment of a wound or incision via the application of a cyanoacrylate material for use on lacerations, incisions and wound sites.

BACKGROUND OF THE INVENTION

In the medical field, there are several methods currently known for use in the treatment and closing of wounds that result from surgical incisions, lacerations, punctures and the like. In particular, devices such as sutures, surgical staples, surgical skin tapes, and adhesives have been used to assist in the closure of different types of wounds. Many of these devices have several shortcomings, however. For example, sutures and surgical staples involve adding additional trauma to the wound since the needle or staple must be passed through tissue on the edges of the wound site. This results in increased scarring due to the fact that the sutures or staples will cause an increase in the tension at the site. When sutures and staples are used, the body responds by increasing the rate of reepithelilization to the wound site. This reepithelilization increases the amount of scarring that develops around the site. Furthermore, in the case of sutures or surgical staples, these items often have to be removed in a second procedure, resulting in added inconvenience and potential discomfort to the patient. Surgical strips, on the other hand, are typically only used for superficial wounds since the adhesives that are used with the strips have a relatively low holding power and will become loose or fall off the site rather easily, particularly when in the presence of moisture.

For these reasons, it has become more common for medical personnel to apply adhesives directly to a wound or incision site. For example, 1-butyl cyanoacrylates, commonly sold under the names Indermil™ and Histacryl Blue™, have been used to aid in the closure of wounds and lacerations. These materials are directly applied to the wound site and permit the wound to heal over time without the use of sutures, surgical staples or surgical skin tapes. The use of 1-butyl cyanoacrylates, however, is also fairly limited. First, 1-butyl cyanoacrylates, although originally in a liquid form, set upon the skin almost immediately. If the medical personnel applying the material apples it incorrectly, he or she will not have the opportunity to remove the material from the patient before it sets. Additionally, 1-butyl cyanoacrylates become very brittle once they are set. at the wound site. As a result, the material cannot flex in conjunction with skin movement. Furthermore, the brittleness of 1-butyl cyanoacrylates prevents the substance from being used on wounds that are longer than about one inch. or 25.4 millimeters in length.

Another type of material that is used in the medical field is 2-octyl cyanoacrylate, which is sold under the commercial name Dermabond™ by Ethicon, Inc. Dermabond™ adhesive is a glue that can be used on any low-tension area of the body for wounds of varying lengths and sizes. Currently, the recommended and approved technique for applying Dermabond™ adhesive to a wound site is to apply three thin layers of Dermabond™ adhesive over the top of the wound. Each layer extends approximately five millimeters to each side of the wound's edge.

2-octyl cyanoacrylate has been found to have superior strength and flexibility when used as a dressing for low-tension wounds. When used on a low-tension wound, 2-octyl cyanoacrylate will decrease the overall surface tension, which in turn reduces the amount of reepitheliliization and scarring at the wound or incision site. When used on a high-tension wound, however, 2-octyl cyanoacrylate may actually increase the amount of tension at the wound site due to the increase in tension that occurs when a recently-opened wound is resealed. In the case where an incision is made, the amount of pressure resulting from resealing the wound will increase significantly. An increase in tension may also occur when the wound is located an area that undergoes a large amount of flexing, such as knee and elbow joints. In fact, it is possible that using 2-octyl cyanoacrylate at a high tension wound site via conventional methods may result in more scarring than would otherwise occur through the use of sutures. Furthermore, the use of 2-octyl cyanoacrylate via conventional methods can also result in dehiscence of the wound at the edge of the dressing material.

Additionally, when 2-octyl cyanoacrylate is used in a conventional manner, users often have a tendency to pick at the edge of the surface around the wound, resulting in the material peeling away from the wound site and impeding the healing process. This is particularly problematic in the case of pediatric patients, mentally ill patients and the elderly, all of whom may be more likely to pick at the wound covering.

SUMMARY OF THE INVENTION

A method for forming an incision or wound dressing comprises the application of first, second, and third layers 2-octyl cyanoacrylate adhesive to a wound or incision site, with each layer covering the site and extending to at least about five millimeters from each side of the site. After the first, second, and third layers are allowed to polymerize, a fourth layer of 2-octyl cyanoacrylate adhesive is applied, the fourth layer substantially covering at least one millimeter of the extending edge of the first, second, and third layers. In the case of a high-tension wound or a wound near a joint, the fourth layer extends at least about ten millimeters from each side of the site, and a fifth layer of 2-octyl cyanoacrylate adhesive is applied. The fifth layer substantially covers at least one millimeter of the extending edge of the first, second, and third layers and extends from each side of the site a distance less than the distance the fourth layer extends from each side of the site. A similar method may be used for pediatric cases in order to prevent the patient from picking off the adhesive. This method involves the use of four 2-octyl cyanoacrylate layers.

It is therefore an object to the invention to provide an improved method for applying an adhesive material to a wound or incision site.

It is a further object of the invention to provide a method of treating a wound or incision with a cyanoacrylate material that reduces or minimizes the amount of scarring around the site.

It is still another object of the invention to provide a method of applying a cyanoacrylate material to a wound site that reduces or minimizes dehiscence around the wound site.

It is yet another object of the present invention to provide a method for applying a cyanoacrylate material to a high-tension wound or incision site that will reduce or minimize the occurrence of scarring and/or dehiscence around the site.

Finally, it is another object of the present invention to provide a method of applying a cyanoacrylate material to a wound site, such that an individual will have increased difficulty picking or peeling the material away from the wound site.

These and other objects, advantages and features of the invention, together with organization and manner of operation thereof, will become apparent from the following detailed description when taken into conjunction with the accompanying drawings, wherein like elements have like numerals throughout the drawings described below.

DETAILED DESCRIPTION OF THE INVENTION

Figure 1:
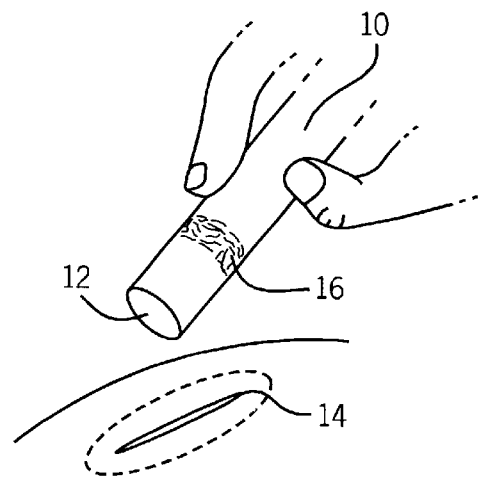
FIG. 1 is an isometric view showing the application of 2-octyl cyanoacrylate to a wound site.

According to the present invention, the treatment of a wound or laceration comprises the use of the adhesive material 2-octyl cyanoacrylate. This topical skin adhesive is sold under the commercial name Dermabond™ and is applied to a wound site, shown as 14 in FIG. 1, through the use of an applicator 10. A vial (not shown) inside the applicator 10 stores the unused 2-octyl cyanoacrylate 16 until application, and the material is applied to the wound 14 via the applicator tip 12. While in the applicator 10, the unused 2-octyl cyanoacrylate 16 is in liquid form. The material will quickly set after it is applied to the wound site 14.

Under the present invention, 2-octyl cyanoacrylate adhesive can be applied to either low or high tension wounds, including areas at or near a joint such as an elbow or knee. In the case where the wound, laceration or incision site is located at or near a joint, the joint should preferably be flexed to about a 45-degree angle in order to compensate for any stretching of the joint that may occur.

Figure 2:
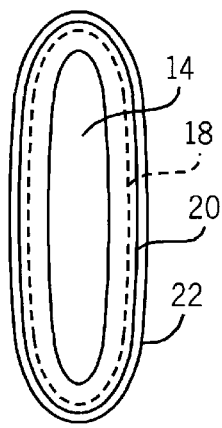
FIG. 2 is a top view of a wound after the first three layers of 2-octyl cyanoacrylate have been applied to the wound site.
Figure 3:
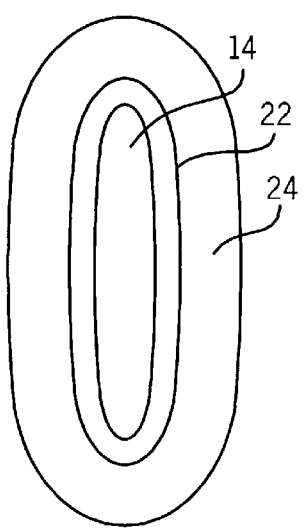
FIG. 3 is a top view of the wound after a fourth layer of 2-octyl cyanoacrylate has been applied to the wound site.
Figure 4:
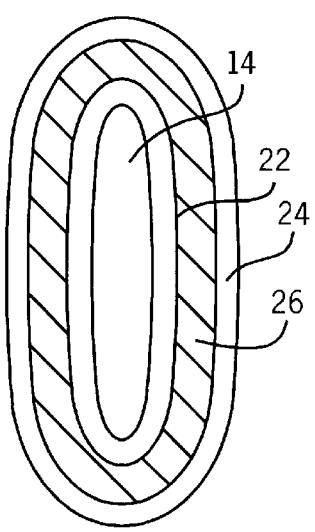
FIG. 4 is a top view of the wound after a fifth layer has been applied to the wound site.
Figure 5:
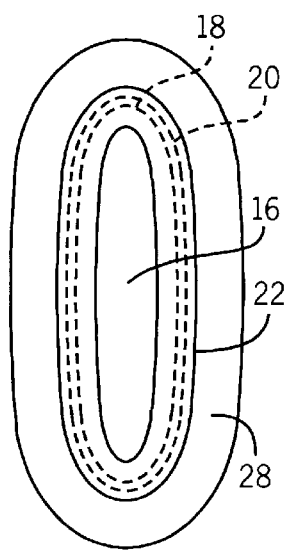
FIG. 5 is a top view of a wound in a pediatric case, wherein each of the layers of 2-octyl cyanoacrylate has been applied to the wound site.

A method for applying 2-octyl cyanoacrylate to a wound site is shown in detail in FIGS. 2–4. After the wound site 14 is defined and cleaned, the user squeezes the applicator 10, causing some unused material 16 to seep through the applicator tip 12. The user then applies multiple layers of 2-octyl cyanoacrylate to the wound site or incision line 14. Preferably, three separate layers 18, 20 and 22 of material are applied to the wound or incision site 14, with none of the layers 18, 20 and 22 extending more than about five millimeters away from the nearest edge of the site 14. The second layer 20 is preferably applied to the site 14 about ten to fifteen seconds after the first layer 18 has been applied, and the third layer 22 is preferably applied about ten to fifteen seconds after the second layer 20 has been applied. Before and while applying the layers 18, 20, and 22, the user may approximate the wound edges with their fingers while wearing latex-free gloves.

After the third layer 22 of 2-octyl cyanoacrylate is applied to the wound site, the first, second, and third layers 18, 20 and 22 are allowed to set and polymerize. After about forty-five seconds have elapsed since the beginning of application of the first layer 18, a fourth layer 24 of 2-octyl cyanoacrylate is applied to the site 14. The fourth layer 24 will begin just inside the five millimeter edge of the third layer 22. The fourth layer 24 will extend at least about seven millimeters from the nearest edge of the site 14. In one embodiment, the fourth layer 24 should extend at least about ten millimeters from the nearest edge of the wound site 14. It is important that at least one millimeter of the extending edge of the original 2-octyl cyanoacrylate layers 18, 20 and 22 be covered by the fourth layer 24 of 2-octyl cyanoacrylate. Under this arrangement, the fourth layer 24 begins about four millimeters from each side of the wound site 14. This application allows the tension, created by the layers, to be more evenly distributed across the material covering the wound site 14.

After the fourth layer 24 of 2-octyl cyanoacrylate is applied to the wound site 14, the user waits at least about fifteen additional seconds in order to allow the fourth layer 24 to properly set and polymerize. After this additional fifteen seconds, a fifth layer 26 of 2-octyl cyanoacrylate is applied to the wound site 14. The fifth layer 26 preferably extends no more than about nine millimeters from the nearest edge of the site 14 and also covers at least about one millimeter of the extending edge of the original 2-octyl cyanoacrylate layers 18, 20 and 22. This placement also aids in more evenly distributing the tension created by the 2-octyl cyanoacrylate while increasing the overall strength of the dressing. Using this application, it is important that the fifth layer 26 not extend as far as the fourth layer 24 from the wound site in any direction.

Additionally, there are other variations to the method previously described for applying 2-octyl cyanoacrylate to a wound, incision or laceration site 14. For example, before the fifth layer 26 of 2-octyl cyanoacrylate is applied to the site 14 an additional layer of 2-octyl cyanoacrylate (not shown) may be applied to the site 14, covering the same general area as the fourth layer 24. This additional layer may aid in strengthening the entire wound dressing and helping to distribute the tension across the dressing. Additionally, it is possible to extend the fourth and fifth layers 24 and 26 by at least about five additional millimeters in each direction from the edge of the site 14. In one embodiment, the fourth layer 24 extends to at least about 17 millimeters from each side of the site 14, while the fifth layer 26 will extend to at most about fourteen millimeters from the wound site 14. The enlarged surface area created by this application decreases the surface tension on the dressing.

In addition to the above, there is also an alternative method for applying 2-octyl cyanoacrylate to a wound site 14. This method may be used in situations such as pediatric cases or cases involving the elderly or individuals suffering from mental illness. This method has the added benefit of reducing the ability of patients to pick at the wound dressing. This method also aids at reducing dehiscence around the wound edges. This method involves applying three layers 18, 20 and 22 of 2-octyl cyanoacrylate to the wound, laceration or incision site 14. This is done in a manner similar to the method described in FIGS. 2–4.

After the three layers 18, 20 and 22 are applied in about ten second intervals and are allowed to set and polymerize for a total of about forty-five seconds from the beginning of the first application, an additional layer 28 of 2-octyl cyanoacrylate is applied to the site 14. The additional layer 28 starts at about the five millimeter edge of the first, second and third layers 18, 20 and 22, and extends until it is no less than about seven millimeters from the incision site 14. In one embodiment of the invention, the additional layer 28 extends to at least about ten millimeters from the site 14. As in the previously described methods, it is important that the additional layer 28 cover at least about one millimeter of the extending edge of the original 2-octyl cyanoacrylate layers 18, 20 and 22. This additional layer 28 effectively glues down the original layers 18, 20 and 22, preventing the patient from picking off any of the original layers 18, 20 and 22.

While preferred embodiments have been shown and described, it should be understood that changes and modifications can be made therein without departing from the invention in its broader aspects. For example, it is possible that the 2-octyl cyanoacrylate could be applied in slightly different locations relative to the wound site, or that a different number of layers could be used to create an effective dressing. Furthermore, it is possible that other materials with properties similar to 2-octyl cyanoacrylate could be used on a wound or incision site while still creating an effective wound dressing in accordance with the invention's broader aspects. Various features of the invention are defined in the following claims:

What is claimed is:

1. A method for forming an incision or wound dressing which method comprises:
   applying a first layer of cyanoacrylate adhesive to a wound or incision site, the first layer extending beyond each side of the site;
   applying a second layer of cyanoacrylate adhesive to the site, the second layer substantially covering the first layer of cyanoacrylate adhesive;
   applying a third layer of cyanoacrylate adhesive to the site, the third layer substantially covering the second layer of cyanoacrylate adhesive;
   polymerizing the first, second, and third cyanoacrylate layers over the site; and
   applying a fourth layer of cyanoacrylate adhesive, the fourth layer covering the extending edge of the first, second, and third layers.

2. The method of claim 1, wherein the first layer extends to at most about five millimeters from each side of the site.

3. The method of claim 2, wherein the fourth layer begins about four millimeters from each side of the site and extends to at least about seven millimeters from each side of the site.

4. The method of claim 3, wherein the cyanoacrylate adhesive is 2-octyl cyanoacrylate adhesive.

5. The method of claim 4, further comprising the steps of:
   polymerizing the fourth cyanoacrylate layer; and
   applying a fifth layer of cyanoacrylate adhesive, the fifth layer beginning about four millimeters from each side of the site and extending from each side of the site a distance less than the distance the fourth cyanoacrylate extends from each side of the site.

6. The method of claim 5, wherein the fourth layer extends to at least about ten millimeters from each side of the site.

7. The method of claim 6, further comprising, before polymerizing the fifth cyanoacrylate layer, applying a sixth layer of cyanoacrylate adhesive to the site, the sixth layer substantially covering the fourth cyanoacrylate layer.

8. The method of claim 7, wherein the sixth layer begins about four millimeters from each side of the site and extends at least about ten millimeters from each side of the site.

9. The method of claim 5, wherein the fourth layer extends to at least about seventeen millimeters from each side of the site.

10. The method of claim 9, wherein the fifth layer extends at most than about fourteen millimeters from each side of the site.

11. The method of claim 5, wherein the fifth layer extends at most about nine millimeters from each side of the site.

12. The method of claim 5, wherein the wound is located in the general vicinity of a joint, and further comprising the step of, before applying the first layer, flexing the joint to about a forty-five degree angle.

13. A method of treating a wound or laceration which method comprises:
   applying a first layer of 2-octyl cyanoacrylate adhesive to a wound or incision site, the first layer extending beyond each side of the site;
   applying a second layer of 2-octyl cyanoacrylate adhesive to a wound or incision site, the second layer extending beyond each side of the site;
   applying a third layer of 2-octyl cyanoacrylate adhesive to a wound or incision site, the third layer extending beyond from each side of the site;
   allowing the first, second, and third 2-octyl cyanoacrylate layers to polymerize; and
   applying a fourth layer of 2-octyl cyanoacrylate adhesive, the fourth layer substantially covering at least about one millimeter of the extending edge of the first, second, and third layers.

14. The method of claim 13, wherein the fourth layer extends at least about seven millimeters from each side of the site.

15. The method of claim 14, wherein the first, second, and third layers extend to at most about five millimeters from each side of the site.

16. The method of claim 15, further comprising the steps of:
   allowing the fourth layer to polymerize over the site; and
   applying a fifth layer of 2-octyl cyanoacrylate adhesive, the fifth layer substantially covering at least one millimeter of the extending edge of the first, second, and third layers and extending from each side of the site a distance less than the distance the fourth layer extends from each side of the site.

17. The method of claim 16, wherein the fourth layer extends at least about ten millimeters from each side of the site.

18. The method of claim 17, further comprising the step of, before polymerizing the fifth layer, applying a sixth 2-octyl cyanoacrylate layer, the sixth layer substantially covering at least one millimeter of the extending edge of the first, second, and third layers and substantially covering the fourth 2-octyl cyanoacrylate layer.

19. The method of claim 16, wherein the fourth layer extends to at least about seventeen millimeters from each side of the site.

20. The method of claim 19, wherein the fifth layer extends to at most about fourteen millimeters from each side of the site.

21. The method of claim 16, wherein the fifth layer extends to at most about nine millimeters from each side of the site.

22. The method of claim 13, wherein the wound is located in the general vicinity of a joint, and further comprising the step of, before applying the first layer, flexing the joint to about a forty-five degree angle.

23. A dressing for a wound or incision, comprising:
   a first layer of 2-octyl cyanoacrylate adhesive adapted to cover a wound or incision site, the first layer adapted to extend beyond each side of the site;

a second layer of 2-octyl cyanoacrylate adhesive adapted to cover the site, the second layer placed over the first layer and adapted to extend beyond each side of the site;

a third layer of 2-octyl cyanoacrylate adhesive adapted to cover the site, the third layer placed over the second layer and adapted to extend beyond each side of the site;

a fourth layer of 2-octyl cyanoacrylate adhesive covering at least one millimeter of the extending edge of the first, second, and third 2-octyl cyanoacrylate layers; and a fifth layer of cyanoacrylate adhesive substantially covering at least one millimeter of the extending edge of the first, second, and third 2-octyl cyanoacrylate layers and adapted to extend from each side of the site a distance less than the distance the fourth cyanoacrylate extends from each side of the site, wherein the fourth layer is adapted to extend at least about ten millimeters from each side of the site, the first, second, and third layers adapted to extend to at most about five millimeters from each side of the site.

24. The dressing of claim 23, wherein the fourth layer is adapted to extend to at least about twelve millimeters from each side of the site.

25. The dressing of claim 24, further comprising a sixth 2-octyl cyanoacrylate layer substantially covering at least about one millimeter of the extending edge of the first, second, and third 2-octyl cyanoacrylate layers and substantially covering the fourth 2-octyl cyanoacrylate layer, the sixth layer located between the fourth and fifth layers.

26. The dressing of claim 23, wherein the fourth layer is adapted to extend to at least about seventeen millimeters from each side of the site.

27. The dressing of claim 26, wherein the fifth layer is adapted to extend to at most about fourteen millimeters from each side of the site.

28. The dressing of claim 23, wherein the fifth layer is adapted to extend to at most about nine millimeters from each side of the site.

* * * * *